(12) United States Patent
Frater et al.

(10) Patent No.: US 6,297,211 B1
(45) Date of Patent: Oct. 2, 2001

(54) ODORANT COMPOSITIONS

(75) Inventors: Georg Frater, Winterthur; Philip Kraft; Urs Müller, both of Dübendorf, all of (CH)

(73) Assignee: Givaudan Roure (International) SA, Geneve (CH)

( * ) Notice: Subject to any disclaimer, the term of this patent is extended or adjusted under 35 U.S.C. 154(b) by 0 days.

(21) Appl. No.: 09/502,683

(22) Filed: Feb. 11, 2000

(30) Foreign Application Priority Data

Feb. 19, 1999 (EP) .................................................. 99103243

(51) Int. Cl.$^7$ ....................................................... A61K 7/46
(52) U.S. Cl. ............................................................ 512/215
(58) Field of Search ................................................ 512/25

(56) References Cited

U.S. PATENT DOCUMENTS 3,959,396    5/1976    Ochsner ................................ 568/840

FOREIGN PATENT DOCUMENTS

| 338895 | 6/1904 | (FR) . |
| 1167776 | 10/1969 | (GB) . |
| 1562796 | 10/1969 | (FR) . |
| WO 98/47842 | 10/1998 | (WO) . |

OTHER PUBLICATIONS

Harder, U., et al., *Recent Developments in Flavor and Fragrance Chemistry*, 147–164, (1993).

Frater, G. et al., *Tetrahedron*, 54, 7633–7703, (1998).

*Primary Examiner*—Jill Warden
*Assistant Examiner*—Monique T. Cole
(74) *Attorney, Agent, or Firm*—Stephen M. Haracz; Kevin C. Hooper; Bryan Cave LLP

(57) ABSTRACT

The invention includes (6E)- and (6Z)-isomers of 3,6-dimethyloct-6-en-1-ols and 6-ethyl-3-methyloct-6-en-1-ols and their mixtures. The mixtures are free from their corresponding oct-5-ene double bond isomers. Processes of preparing odorant compositions containing these compositions are also provided.

11 Claims, No Drawings

ODORANT COMPOSITIONS

FIELD OF THE INVENTION

The invention relates to (6E)- and (6Z)-isomers of 3,6-dimethyloct-6-en-1-ols and 6-ethyl-3-methyloct-6-en-1-ols and mixtures thereof as well as the use of these mixtures in odorant compositions. The mixtures are free from their corresponding oct-5-ene double bond isomers.

BACKGROUND OF THE INVENTION

Although it has previously not been known that one compound alone can imitate true to nature the complex olfactory impression of lily of the valley, hydroxycitronellal (3,7-dimethyl-7-hydroxyoctan-1-al) comes remarkably close to the odor of lily of the valley. In combination with other lily of the valley odorants such as LYRAL® (4-(4-hydroxy-4-methylpent-1-yl)-cyclohex-3-ene-1-carboxaldelhyde), LILIAL® (3-(4-tert-butylphenyl)-2-methylpropanal) and/or DUPICAL® (4-(octahydro-4,7-methano-5H-inden-5-ylidene)butanal) (G. Frater, J. A. Bajgrowicz, P. Kraft, Fragrance Chemistry, Tetrahedron 1998, 54, 7633–7703) it is, however, possible to come very close to the natural standard. The aldehyde group is common to all of these mentioned odorants with lily of the valley character. This gives rise to an instability of the compounds in oxidizing or strongly alkaline media.

Some lily of the valley odorants without an aldehyde function have been found in the alcohols MAYOL® (4-(1-methylethyl)cyclohexylmethanol), MAJANTOL® (2,2-dimethyl-3-(3-methylphenyl)propanol), FLOROL® (tetrahydro-4-methyl-2-(2-methylpropyl-2H-pyran-4-ol) and MUGETANOL® (U. Harder, E. Oelkers, in: Recent Developments in Flavor and Fragrance Chemistry, published by VCH, Weinheim, 1993, pp. 162–163). Moreover, the carbon analogue to FLOROL® with very similar olfactory properties to FLOROL® has become known from WO 98/47842. However, these alcohols possess neither the naturalness, radiating strength and crispness nor the olfactory strength of the aforementioned aldehydes, and the need for a replacement substance for the lily of the valley aldehydes therefore continues to exist. There is therefore a requirement for additional lily of the valley odorants, especially with a functional group other than the aldehyde function, in order to obviate the previously mentioned disadvantages.

In GB Patent No. 1,167,776 claim is made, inter alia, to supposed compounds of general formulae Ia and Ib.

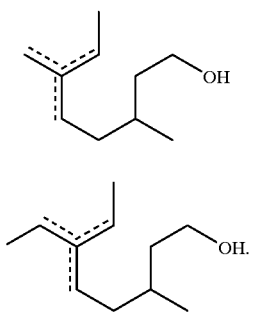

Ia

Ib

From the examples given therein it is, however, evident that compounds falling within formulae Ia and Ib were never prepared in pure form. It has now been established that this is also not at all possible on the basis of the route of preparation described. In fact, in the dehydration of the 1,6-diols which are the basis for the compounds Ia and Ib there is obtained a mixture of all three possible isomeric octan-1-ols with respect to the double bond. For example, in the case of compounds Ib there are obtained according to the given process the alcohols (6E)-6-ethyl-3-methyloct-6-en-1-ol (ca. 30%), (6Z)-6-ethyl-3-methyloct-6-en-1-ol (ca. 30%) and 6-ethyl-3-methyloct-5-en-1-ol (ca. 40%). As mentioned in the patent, this mixture of compounds Ib has, in fact, the indicated odor of lily of the valley and rose, but the odor of the rose side notes is unpleasantly musty. Because of this musty rose-like side note, the mixture Ib cannot completely satisfy the requirements of a lily of the valley odorant without an aldehyde function. It has therefore been used in perfumery only sporadically. Today, there is practically no commercial demand for this mixture. The production of the mixture Ib has in the meanwhile been discontinued for this reason.

SUMMARY OF THE INVENTION

It has now surprisingly been found that the undesired must) rose-like side notes of the mixtures Ia and Ib is due to the oct-5-en-1-ols 6-ethyl-3-methyloct-5-en-1-ol and (5E/Z)-3,6-dimethyloct-5-en-1-ol and that in the absence of these compounds there are obtained mixtures which do not have the aforementioned disadvantages. One object of the invention is, therefore, a composition containing a mixture of the following compounds:

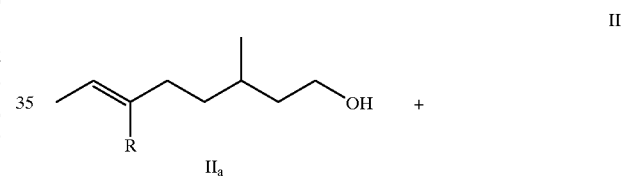

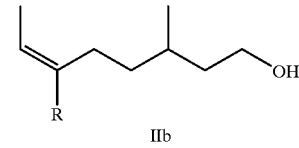

wherein R is a methyl or ethyl group. In the present invention, the composition includes all R- and S-enantiomers of the compounds. The class of compositions in the present invention accordingly embraces the compounds $II_{1a}$, $II_{1b}$, $II_{2a}$, and $II_{2b}$ and their mixtures ($II_1$ and $II_2$).

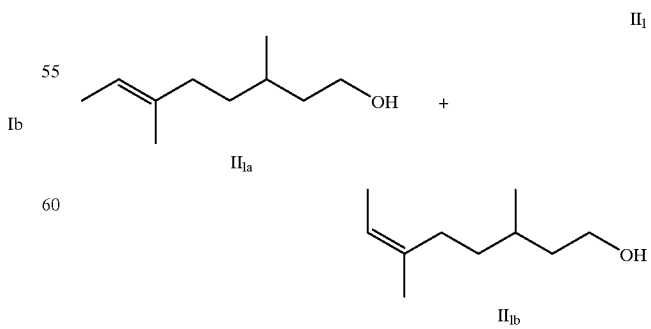

-continued

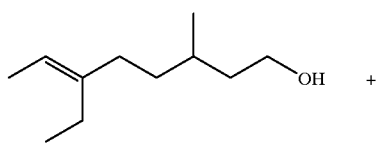

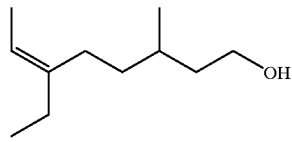

Accordingly, one embodiment of the invention is a composition that includes a mixture of compounds having the formula II:

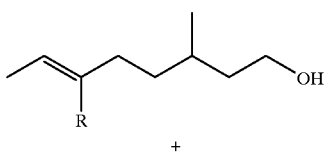

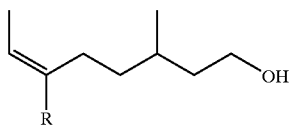

wherein R is methyl or ethyl and which composition is free from the corresponding oct-5-ene double bond isomers. These compositions may be R- and S-enantiomers.

The invention includes a composition containing a mixture of compounds (6E)-3,6-dimethyloct-6-en-1-ol and (6Z)-3,6-dimethyloct-6-en-1-ol (II$_1$):

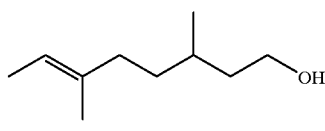

which composition is free from (5E/Z)-3,6-dimethyloct-5-en-1-ol.

The invention also includes a composition containing a mixture of compounds (6E)-6-ethyl-3-methyloct-6-en-1-ol and (6Z)-6-ethyl-3-methyloct-6-en-1-ol (II$_2$):

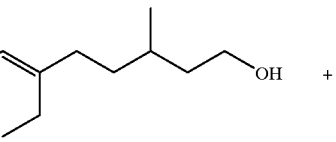

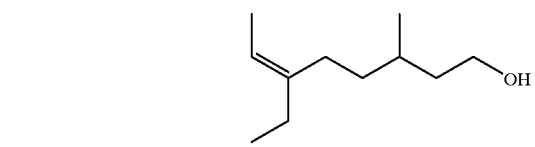

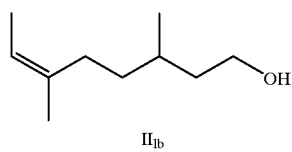

which composition is free from (5E/Z)-ethyl-3-methyloct-5-en-1-ol.

Other embodiments of the invention include odorant compositions containing compositions II, II$_1$, and II$_2$ as defined above.

The invention also provides a process for preparing an odorant composition for use in a perfume or cosmetic composition that includes mixing an effective amount of compositions II, II$_1$, or II$_2$ as defined above with a perfume or cosmetic base.

DETAILED DESCRIPTION OF THE INVENTION

The composition II$_1$ of the present invention has a floral, crisp-aldehydic odor typical of lily of the valley with, surprisingly, a delicate citric nuance and a threshold value of 10 ng/l air. More surprising, however, is the fact that the composition II$_2$ has an extremely uniform and independent, specific lily of the valley fragrance, floral, crisp-aldehydic, with an even somewhat lower threshold value than composition II$_1$, namely of 6 ng/l air.

The musty-rose like aspects of the mixtures Ia and Ib of the prior art are no longer present in the compositions of the present invention. Thus, independent fragrance notes may now be created. The compositions II$_1$ and II$_2$ of the present invention are therefore ideally suited—unlike the mixtures Ia and Ib—as lily of the valley odorants without an aldehyde function, which surpass the known aldehyde substitutes in radiating strength, crispness, and olfactory uniformity. The citric olfactory nuance of the composition II$_1$ is a surprising new occurrence, which was not previously recognized in the mixtures Ia and Ib according to GB Patent No. 1,167,776, because it was masked by the musty rose-like note.

The compositions II$_1$ and II$_2$ or their mixtures are thus outstandingly suitable for perfumes of the crisp-flowery type, especially of the so-called Eaux Fraîches, such as, for example, Eau d'Eden (Cacharel, 1996), Eau d'Issey (I. Miyake, 1997), Eau belle (L. Azzaro, 1995), Eternity (C. Klein, 1988), Escape (C. Klein, 1991), New West for her (Aramis, 1990), and particularly those with an accentuated lily of the valley character, such as, for example, Diorissimo (Dior, 1956), Pleasures (E. Lauder, 1995), Aqua di Gio (Armani, 1994), Hugo Woman (H. Boss, 1997), Envy (Gucci, 1996), Polo Sport Woman (R. Lauren, 1996).

The use of compositions of the present invention is, however, limited neither to these perfume types, nor to special olfactory directions, odorants, or substance classes. The following are set forth as non-limiting examples of substance classes which harmonize especially well with the compositions in accordance with the invention.

| | |
|---|---|
| Ethereal Oils and Extracts | Bergamot oil, cedarwood oil, galbanum oil, jasmine absolute, rose oil, ylang-ylang oil. |
| Alcohols | Citronellol, DIMETOL ®, dimethylphenyl-ethyl carbinol, EBANOL ®, ethyllinalool, geraniol, PEONIL ®, phenylethyl alcohol, RADJANOL ®, UNDECAVERTOL ® |
| Aldehydes and Ketones | ADOXAL ®, alpha-damascone, DUPICAL ®, FLORHYDRAL ®, HEDIONE ®, hydroxycitronellal, cis-jasmone, LILIAL ®, LYRAL ®, 4-(4-methoxyphenyl)-butan-2-one, MYRALDENE ®, NECTARYL ®, SCENTENAL ®, TRICYCLAL ®, TROPIONAL ®, VERTOFIX ® |
| Ethers and Acetals | ACETAL CD ®, AMBROFIX ®, CALONE ®, Diphenyl oxide, FOLENOX ®, GALAXOLIDE ®, GLYCOLIERRAL ®, LIMETTOL ®, MAGNOLAN ®, RHUBAFURAN ®, SPIRAMBRENE ® |
| Esters and Lactones | AGRUMEX ®, benzyl acetate, benzyl salicylate, citronellyl acetate, GARDENOL ®, cis-3-hexenyl salicylate, MYRALDYLACETATE ®, PRUNOLIDE ®, cis-jasmone lactone, JASMONYL ®, gamma-undecalactone |
| Macrocycles | AMBRETTOLIDE ®, AMBRETONE ®, ETHYLENEBRASSYLATE ®, HABANOLIDE ®, MUSCONE ®, MUSK CPD ®, MUSK 174 ®, THIBETOLIDE ® |
| Heterocycles | indole, PYRALONE ® |

The compositions $II_1$ and $II_2$ were produced by the reaction of a Grignard reagent (THP-protected 5-bromo-3-methylpentan-1-ol) with acetaldehyde or propionaldehyde then a Dess-Martin oxidation, followed by a Wittig reaction with ethyltriphenylphosphonium bromide and acid-catalyzed deprotection. Other protecting groups (e.g. tert-butyldimethylsilyl) or oxidizing agents (e.g. pyridinium chlorochromate) can, however, also be employed. This approach, which yields the compounds of the present invention free from the corresponding oct-5-ene double bond isomers, is illustrated in the following Schemes:

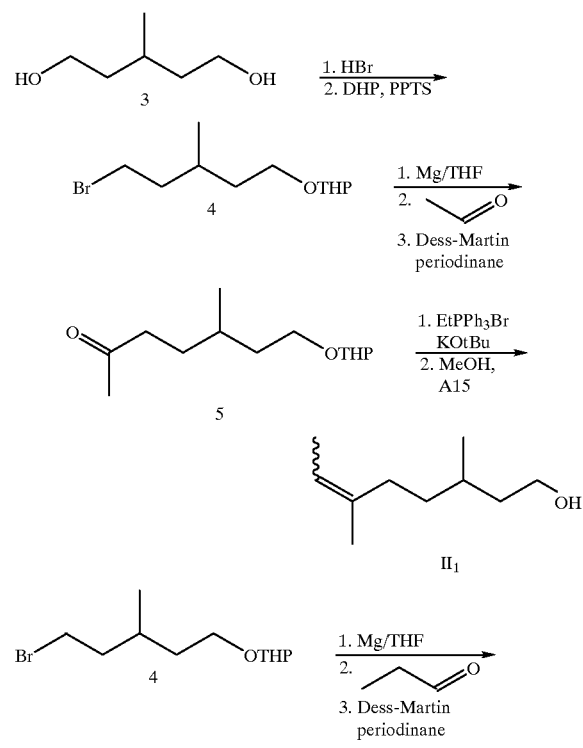

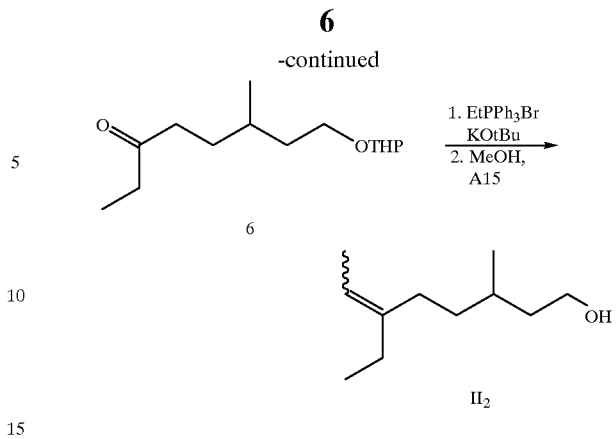

The following examples are provided to further illustrate methods of preparation of the compounds of the present invention, as well as certain physical properties and uses thereof. The examples are illustrative only are not intended to limit the scope of the invention in any way.

EXAMPLE 1

(6E/Z)-3,6-Dimethyloct-6-en-1-ol ($II_1$)

A solution of 182 ml (1.50 mol) of 3-methylpentane-1,5-diol (3) in 3 l of toluene was treated portionwise with a total of 185 ml (1.6 mol) of 48 percent hydrobromic acid and then heated to reflux (internal temperature 100–110° C.) on a water separator for 5 hours. After 170 ml of water had been separated, the reaction mixture was left to cool, poured onto 400 g of ice, and treated with 500 ml of water and 30 ml of 30 percent sodium hydroxide solution. The organic phase was separated and washed with 750 ml of 2N hydrochloric acid, twice with 750 ml of water per wash and then with 750 ml of saturated sodium chloride solution. After drying over sodium sulphate and concentration on a rotary evaporator there were obtained, after flash chromatography (tert-butyl methyl ether:n-pentane, 1:1, $R_f$=0.57) on silica gel, 106 g (39%) of 5-bromo-3-methylpentan-1-ol.

A solution of 1.48 g (0.82 mol) of 5-bromo-3-methylpentan-1-ol from several analogous batches in 1 l of dry dichloromethane was treated with a solution of 107 g (1.27 mol) of 3,4-dihydropyran and 17.4 g (69.3 mmol) of pyridinium toluene-4-sulphonate in 1 l of dry dichloromethane under nitrogen while stirring and cooling in an ice-water bath. After removal of the cooling, the reaction mixture was left to stir at room temperature for a further 8 hours. It was then poured into 6 l of water and the product was extracted twice with 500 ml of tert-butyl methyl ether per extraction. The combined organic extracts were dried over sodium sulphate and freed from solvent on a rotary evaporator. Flash chromatography (n-pentane:tert-butyl methyl ether, 20:1) on silica gel yielded 197 g (91%) of 5'-bromo-3'-methylpent-1'-yl tetrahydropyran-2-yl ether (4).

IR (film): $v$=1035/1077/1121/1135 cm$^{-1}$ ($v$ C—O), 1353/1381 cm$^{-1}$ ($v$ $CH_3$), 1454/1441 cm$^{-1}$ ($v$ $CH_2$).—$^1$H-NMR ($CDCl_3$): $\delta$=0.94 (d, J=6.4 Hz, 3H, 3'-$H_3$), 1.43–1.71 (m, 8H, 3-, 4-, 5-, 2'-$H_2$), 1.82 ($m_c$, 2H, 3'-H, 4'-$H_b$), 1.93 ($m_c$, 1H, 4'-$H_a$), 3.37–3.52 (m, 4H, 1'-, 5'-$H_2$), 3.77–3.87 (m, 2H, 6-$H_2$), 4.57 ($m_c$, 1H, 2-H).—$^{13}$C-NMR ($CDCl_3$): $\delta$=18.83/18.92 (2q, 3'-Me), 19.48 (2t, C-4), 25.35 (2t, C-5), 28.88/28.94 (2d, C-3'), 30.61 (2t, C-3), 31.67 (2t, C-5'), 35.94/36.03 (2t, C-2'), 39.82/39.93 (2t, C-4'), 62.15/62.18 (2t, C-1'), 65.16/65.34 (2t, C-6), 98.62/98.83 (2d, C-2).—MS (EI): m/z (%)=41 (30)($C_3H_5^+$), 55 (63)($C_4H_7^+$), 85 (100) ($C_5H_9O^+$), 101 (3)($C_5H_9O_2^+$, complementary to m/z=163/

165), 163/165 (9)($C_6H_{12}Br^+$, complementary to m/z=101), 263/265 (2)($M^+$-H).

About 5 ml of a solution of 50.0 g (200 mmol) of 5'-bromo-3'-methylpent-1'-yl tetrahydropyran-2-yl ether (4) in 250 ml of dry tetrahydrofuran were added to 5.50 g (226 mmol) of magnesium shavings in 40 ml of dry tetrahydrofuran. The mixture was heated while stirring slowly with a KPG stirrer until the reaction began. Then, the heating source was removed and the remainder of the 5'-bromo-3'-methylpent-1'-yl tetrahydropyran-2-yl ether solution was slowly added dropwise. Subsequently, the mixture was heated under reflux for 20 hours and, after cooling, a solution of 11.0 g (250 mmol) of acetaldehyde in 70 ml of dry tetrahydrofuran was slowly added dropwise. After stirring for 3 hours, the reaction mixture was added to 1 l of saturated ammonium chloride solution, the organic phase was separated, and the aqueous phase was extracted twice with 300 ml of tert-butyl methyl ether each time. The combined organic phases were washed twice with 300 ml of saturated sodium chloride solution each time, dried over sodium sulphate and concentrated to dryness on a rotary evaporator.

By flash chromatography (n-pentane:tert-butyl methyl ether, 5:1, $R_f$=0.30) of the residue on silica gel there were obtained 26.5 g (58%) of 5'-methyl-2'-hydroxyhept-7'-yl tetrahydropyran-2-yl ether. This was taken up in 350 ml of dry dichloromethane and treated at room temperature with a solution of 73.1 g (173 mmol) of Dess-Martin periodinate in 350 ml of dry dichloromethane. After stirring at room temperature for 2 hours the reaction mixture was treated with 1 l of tert-butyl methyl ether and a solution of 225 g (1.42 mmol) of sodium thiosulphate in 1 l of saturated sodium hydrogen carbonate solution. After stirring at room temperature for 10 minutes the organic phase was separated, the aqueous phase was extracted twice with 500 ml of tert-butyl methyl ether each time and the combined organic phases were washed with saturated sodium hydrogen carbonate solution and saturated sodium chloride solution. After drying over sodium sulphate and removal of the solvent on a rotary evaporator, there were obtained by flash chromatography (n-pentane:tert-butyl methyl ether, 10:1, $R_f$=0.42) on silica gel 23.1 g (88%) of 5'-methyl-2'-oxohept-7'-yl tetrahydropyran-2-yl ether (5).

IR (film): $\nu$=1717 $cm^{-1}$ ($\nu$ C=O), 1035/1078/1122/1136 $cm^{-1}$ ($\nu$ C—O), 1355 $cm^{-1}$ ($\nu$ $CH_3$), 1454/1441 $cm^{-1}$ ($\nu$ $CH_2$).—$^1$H-NMR ($CDCl_3$): $\delta$=0.91 (d, J=5.6 Hz, 3H, 5'-$H_3$), 1.43–1.81 (m, 11H, 3-$H_2$–5-$H_2$ and 4'-$H_2$–6'-$H_2$), 2.15 (s, 3H, 1'-$H_3$), 2.42–2.48 (m, 2H, 3'-$H_2$), 3.38–3.53 (m, 2H, 7'-$H_2$), 3.74–3.88 (m, 2H, 6-$H_2$), 4.56/4.57 (2t, J=4.2/4.0 Hz, 1H, 2-H).—$^{13}$C-NMR ($CDCl_3$): $\delta$=19.17/19.28 (2q, C-1'), 19.47/19.52 (2q, 5'-Me), 25.27 (2t, C-5), 29.37/29.41 (2d, C-5'), 30.48/30.57 (2t, C-3), 36.18/36.22 (2t, C-6'), 41.14/41.11 (2t, C-3'), 62.14/62.21 (2t, C-7'), 65.32/65.51 (2t, C-6), 98.61/98.94 (2d, C-2), 208.97/209.60 (2s, C-2').—MS (EI): m/z (%)=43 (48)($C_3H_7^+$), 55 (15)($C_4H_7^+$), 69 (27) ($C_5H_9^+$), 85 (100)($C_5H_9O^+$), 101 (18)($C_8H_{15}O^+$, complementary to m/z=127), 109 (43)($C_8H_{13}^+$), 127 (35)($M^+$-$C_8H_{15}O$, complementary to m/z=101), 143 (8)($M^+$-$C_5H_9O$), 227 (1)($M^+$-H).

14.7 g (39.5 mmol) of ethyltriphenylphosphonium bromide were added under nitrogen to a solution of 4.25 g (37.8 mmol) of potassium tert-butylate in 50 ml of dry tetrahydrofuran. The reaction mixture was heated to reflux and at this temperature a solution of 7.50 g (32.9 mmol) of 5'-methyl-2'-oxohept-7'-yl tetrahydropyran-2-yl ether (5) in 25 ml of dry tetrahydrofuran was allowed to drop in. After stirring under reflux for 2 hours and at room temperature for 8 hours the reaction mixture was added to 400 ml of tert-butyl methyl ether/water (1:1), the organic phase was then separated and the aqueous phase was extracted three times with 100 ml of tert-butyl methyl ether each time. The organic phases were combined, dried over sodium sulfate, and concentrated on a rotary evaporator.

By flash chromatography (n-pentane:tert-butyl methyl ether, 100:1, $R_f$=0.44) on silica gel there were obtained 7.15 g (90%) of 3',6'-dimethyloct-2'-en-8'-yl tetrahydropyran-2-yl ether as a colorless liquid. A solution of 7.00 g (29.1 mmol) of the 3',6'-dimethyloct-2'-en-8'-yl tetrahydropyran-2-yl ether in 200 ml of dry methanol was treated with 10 g of AMBERLYST® 15 and stirred for 20 hours at room temperature. The ion exchanger was filtered off and extracted twice with 100 ml of methanol. After concentration of the combined organic phases on a rotary evaporator there were obtained by flash chromatography (n-pentane:tert-butyl methyl ether, 10:1, $R_f$=0.14) 3.86 g (85%) of (6E/Z)-3,6-dimethyloct-6-en-1-ol ($II_1$) as a liquid with an intensive odor.

Odor: Floral, crisp-aldehydic, after lily of the valley with a light citrus nuance.—IR (film): $\nu$=3338 $cm^{-1}$ ($\nu$ C—H), 1059 $cm^{-1}$ ($\nu$ O—H), 1457 $cm^{-1}$ ($\nu$ $CH_2$), 1378 $cm^{-1}$ ($\nu$ $CH_3$).—$^1$H-NMR ($CDCl_3$): $\delta$=0.89/0.90 (2d, J=6.8/6.4 Hz, 3H, 3-Me), 1.26-1.18 (m, 1H, 3-H), 1.35–1.43 (m, 2H, 4-$H_2$), 1.52–1.66 (m, 2H, 2-$H_2$), therein 1.56 (d, J=6.8 Hz, 3H, 8-$H_3$), 1.59/1.67 (2s, 3H, 6-Me), 1.98–2.04 (m, 2H, 5-$H_2$), 2.42 (br s, 1H, OH), 3.61–3.70 (m, 2H, 1-$H_2$), 5.19 ($m_c$, 1H, 7-H).—$^{13}$C-NMR ($CDCl_3$): $\delta$=13.03/13.20 (2q, C-8), 19.44 (2q, 3-Me), 15.48/23.27 (2q, 6-Me), 29.12/29.47 (2d, C-3), 28.70/35.03/35.33/36.93 (4t, C-4,-5), 39.68/39.71 (2t, C-2), 60.79 (2t, C-1), 117.93/118.51 (d, C-7), 136.24/135.96 (2s, C-6).—MS (EI): m/z (%)=41 (100)($C_3H_5^+$), 55 (88)($C_4H_7^+$), 70 (73)($C_5H_{10}^+$), 81 (35)($C_6H_9^+$), 109 (19) ($C_8H_{13}^+$), 123 (4)($M^+$-$H_2O$—$CH_3$), 138 (2)($M^+$-CHO), 156 (8)($M^+$).

EXAMPLE 2

(6E/Z)-6-Ethyl-3-methyloct-6-en-1-ol ($II_2$)

The corresponding Grignard reagent was prepared as described in Example 1 from 1.65 g (67.8 mmol) of magnesium shavings and 18.9 g (67.8 mmol) of 5'-bromo-3'-methylpent-1'-yl tetrahydropyran-2-yl ether (4) in 85 ml of dry tetrahydrofuran. After heating under reflux for 3 hours, the reaction mixture was left to cool to 30° C. and treated dropwise with 4.32 g (74.6 mmol) of propionaldehyde dissolved in 30 ml of dry tetrahydrofuran. After the exothermic reaction had subsided, the mixture was stirred at room temperature for a further 1 hour and then added to 500 ml of saturated ammonium chloride solution. The organic phase was separated and the aqueous phase was extracted three times with 100 ml of tert-butyl methyl ether per extraction. The combined organic phases were washed twice with 150 ml of saturated sodium chloride solution per wash and then dried over sodium sulphate.

After removal of the solvent on a rotary evaporator, there were obtained by flash chromatography (n-pentane:tert-butyl methyl ether, 5:1, $R_f$=0.30) of the residue on silica gel 5.87 g (36%) of 6'-methyl-3'-hydroxyoct-8'-yl tetrahydropyran-2-yl ether. This was dissolved in 75 ml of dry dichloromethane and treated at room temperature with 15.3 g (36.0 mmol) of Dess-Martin periodinate while stirring vigorously. After stirring for 2 hours, 250 ml of tert-butyl methyl ether were added, followed by a solution of 48 g of sodium thiosulphate in 250 ml of saturated aqueous sodium hydrogen carbonate solution. After stirring, for 10 minutes, the organic phase was separated, the aqueous phase was extracted twice with 200 ml of tert-butyl methyl ether, and the combined organic extracts were washed with saturated sodium hydrogen carbonate solution and saturated sodium chloride solution. After drying over sodium sulphate and removal of the solvent on a rotary evaporator there were obtained by flash chromatography (n-pentane:tert-butyl methyl ether, 10:1, $R_f$=0.31) 5.00 g (94%) of 6'-methyl-3'oxooct-8'-yl tetrahydropyran-2-yl ether (6) as a colorless oil.

IR (film): $\nu$=1716 cm$^{-1}$ ($\nu$ C=O), 1034/1078/1122/1136 cm$^{-1}$ ($\nu$ C—O), 1353/1378 cm$^{-1}$ ($\nu$ CH$_3$), 1456 cm$^{-1}$ ($\nu$ CH$_2$).—$^1$H-NMR (CDCl$_3$): $\delta$=0.91 (d, J=6.0 Hz, 3H, 6'-H$_3$), 1.05 (t, J=7.4 Hz, 3H, 1'-H$_3$), 1.41–1.81 (m, 11H, 3-H$_2$-5-H$_2$ and 5'-H$_2$-7'-H$_2$), 2.37–2.48 (m, 4H, 2'-,4'-H$_2$), 3.36–3.53 (m, 2H, 8'-H$_2$), 3.74–3.88 (m, 2H, 6-H$_2$), 4.56/4.57 (2t, J=3.5/4.0 Hz, 1H, 2-H).—$^{13}$C-NMR (CDCl$_3$): $\delta$=7.65 (2q, C-1'), 19.19/19.30 (2q, 6'-Me), 19.48/19.52 (2t, C-4), 25.28 (2t, C-5), 29.44/29.49 (2d, C-6'), 30.57/30.57/30.60/30.67 (4t, C-3,-5'), 35.62/35.64/36.19/36.24 (4t, C-2'-7'), 39.75/39.77 (2t, C-4'), 62.14/62.21 (2t, C-8'), 65.36/65.54 (2t, C-6), 98.62/98.84 (2d, C-2), 211.58/211.59 (2s, C-3').—MS (EI): m/z (%)=57 (53)(C$_4$H$_5$), 85 (100)(C$_5$H$_9$O), 101 (10) (C$_5$H$_8$O), 123 (19)(C$_8$H$_{11}$O), 141 (32)(M$^+$-C$_5$H$_9$O$_2$), 158 (8)(M$^+$-C$_5$H$_8$O), 213 (1)(M$^+$-C$_2$H$_5$O) 241 (1)(M$^+$-H).

As also described in Example 1, 9.10 g (24.6 mmol) of ethyltriphenylphosphonium bromide were added under nitrogen to a solution of 2.60 g (23.2 mmol) of potassium tert-butylate in 40 ml of dry tetrahydrofuran. The reaction mixture was heated to reflux and at this temperature a solution of 9.10 g (24.6 mmol) of 6'-methyl-3'-oxooct-8'-yl tetrahydropyran-2-yl ether (6) in 10 ml of dry tetrahydrofuran was allowed to drop in. After stirring under reflux for 33 hours and at room temperature for 8 hours, the reaction mixture was added to 300 ml of tert-butyl methyl ether/water (1:1). The organic phase was then separated and the aqueous phase was extracted three times with 100 ml of tert-butyl methyl ether per extraction. The organic phases were combined, dried over sodium sulfate, and concentrated on a rotary evaporator.

After flash chromatography (n-pentane:tert-butyl methyl ether, 100:1, $R_f$=0.39) on silica gel there were obtained 4.62 g (96%) of 3'-ethyl-6'-methyloct-2'-en-8'-yl tetrahydropyran-2-yl ether as a colorless liquid. A solution of 4.50 g (18.9 mmol) of the 3'-ethyl-6'-methyloct-2'-en-8'-yl tetrahydropyran-2-yl ether in 150 ml of dry methanol was treated with 7.50 g of AMBERLYST® 15 and stirred for 16 hours at room temperature. The ion exchanger was filtered off and extracted twice with 150 ml of methanol. After concentration of the combined organic phases on a rotary evaporator there were obtained by flash chromatography (n-pentane:tert-butyl methyl ether, 10:1, $R_f$=0.22) 2.52 g (78%) of (6E/Z)-6-ethyl-3-methyloct-6-en-1-ol (II$_2$) as a colorless liquid with an intensive odor.

Odor: Extremely uniform and independent, specifically after lily of the valley, floral, crisp-aldehydic.—IR (film): $\nu$=3328 cm$^{-1}$ ($\nu$ O—H), 1058 cm$^{-1}$ ($\nu$ C—O), 1459 cm$^{-1}$ ($\nu$ CH$_2$), 1377 cm$^{-1}$ ($\nu$ CH$_3$).—$^1$H-NMR (CDCl$_3$): $\delta$=0.90–0.99 (m, 6H, 2'-H$_3$, 3-Me), 1.18–1.26 (m, 1H, 3-H), 1.35–1.45 (m, 2H, 4-H$_2$), 1.51–1.66 (m, 2H, 2-H$_2$), therein 1.57 (d, J=6.8 Hz, 3H, 8-H$_3$), 1.96–2.06 (m, 4H, 5-,1'-H$_2$), 2.15 (br s, 1H, OH), 3.60–3.71 (m, 2H, 1-H$_2$), 5.17 (m$_c$, 1H, 7-H).—$^{13}$C-NMR (CDCl$_3$): $\delta$=12.73/12.74/12.86/12.98 (4q, C-8, C-2'), 19.45/19.48 (2q, 3-Me), 22.62/27.17 (2t, C-1'), 29.27/29.67 (2d, C-3), 29.57/33.87 (2t, C-5), 35.48/35.61 (2t, C-4), 39.69/39.76 (2t, C-2), 60.90 (2t, C-1), 116.78/117.47 (2d, C-7), 141.97 (2s, C-6).—MS (EI): m/z (%)=31 (8)(CH$_2$OH$^+$), 41 (38)(C$_3$H$_5$$^+$), 55 (85)(C$_4$H$_7$$^+$), 69 (84)(C$_5$H$_9$$^+$), 84 (100)(C$_6$H$_{12}$$^+$), 97 (19)(C$_7$H$_{13}$$^+$), 123 (18)(M$^+$-H$_2$O—C$_2$H$_5$), 141 (5)(M$^+$-CHO), 170 (21)(M$^+$).

The compositions containing a mixture of compounds according to formula II are ideally suited for the creation of crisp-flowery lily of the valley accords, as is demonstrated hereinafter in Example 3. The compositions, especially the composition containing the mixture of compounds according to formula II$_1$ (i.e., II$_a$ and II$_{1b}$), intensify the floral base accord.

The compositions defined by formula II, especially the composition defined by formula II$_1$, are likewise ideally suited for use in cosmetic articles and body care agents, especially shower gels and foam baths, for the emphasis of a floral, crisp-aldehydic specific olfactory impression of lily of the valley, whereby the odorant mixture in accordance with the invention does not lead to skin irritations or discoloration. On the other hand, the lily of the valley aldehydic odorants of the state of the art also frequently cause discoloration in addition to skin irritations.

EXAMPLE 3

Unisex Eau Fraîche

Unisex Eau Fraîche with hesperidic top notes, a clean-flowery middle note with lily of the ionone and jasmine bouquet as well as green, crisp-marine accents and an amber like-base note with reminiscences of iris and sandalwood was prepared as follows:

| | Compound/Ingredient | Parts by weight in % |
|---|---|---|
| 1 | Allylcyclohexylglycolate, 10% in dipropylene glycol | 20 |
| 2 | Bergamot oil | 150 |
| 3 | 3-Butyltetrahydro-5-methyl-2H-pyran-4-yl acetate (JASMONYL ®) | 50 |
| 4 | Lemon oil, Italian | 25 |
| 5 | 2,6-Dimethylheptan-2-ol (DIMETOL ®) | 35 |
| 6 | 3,7-Dimethylnona-1,6-dien-3-ol (ethyl linalool) | 50 |
| 7 | Dipropylene glycol | 60 |
| 8 | FLORHYDRAL ®, 10% in dipropylene glycol | 5 |
| 9 | 1,3,4,6,7,8-Hexahydro-4,6,6,7,8,8-hexamethyl-cyclopenta(g)-2-benzopyran (GALAXOLIDE ®) 50 PHT | 100 |
| 10 | Cis-Hex-3-en-1-ol, 10% in dipropylene glycol | 5 |
| 11 | Beta-Ionone | 35 |
| 12 | Spearmint oil, USA, 10% in dipropylene glycol | 5 |
| 13 | Mandarin oil, Italian | 10 |
| 14 | 7-Methyl-2H-1,5-benzodioxepin-3(4H)-one (CALONE 1951 ®), 10% in dipropylene glycol | 5 |
| 15 | Methyl dihydrojasmonate | 200 |
| 16 | 1-Methyl-3-(4-(1,1-dimethylethyl)phenyl)propanal (LILIAL ®) | 35 |
| 17 | 3-Methyl-5-(2,2,3-trimethyl-3-cyclopenten-1-yl)-4-penten-2-ol (EBANOL ®), 10% in dipropylene glycol | 30 |
| 18 | 1-(1,2,3,4,5,6,7,8-Octahydro-1,2,8,8-tetramethyl-2-naphthalenylethanone (GEORGYWOOD ®) | 30 |
| 19 | 3a,6,6,9a-Teramethyldodecahydro(2,1b)naphthofuran (FIXAMBRENE ®), 10% in dipropylene glycol | 75 |
| 20 | Tropional | 25 |
| 21 | Mixture II$_1$ | 50 |
| | | 1000 |

The floral base accord is intensified by the compositions containing a mixture of compounds according to formula II$_1$ (i.e., compounds II$_{1a}$ and II$_{1b}$). The composition confers to the floral base accord a crisp, intensive lily of the valley note without musty side aspects as, for example, when the compound Ia or Ib is used. Thus, the transparent, tea-like facets of the composition according to the present invention come into play especially well.

EXAMPLE 4

Crisp-flowery Perfume Composition for use in Cosmetic Articles and Body Care Agents A crisp-flowery perfume composition was prepared as follows:

| | Compound/Ingredient | Parts by Weight in 1/1250 |
|---|---|---|
| 1 | Ethyl acetoacetate | 25 |
| 2 | Allylcyclohexylglycolate | 2 |
| 3 | Benzyl acetate, purest | 35 |
| 4 | Cassis Base 345 F | 5 |
| 5 | Cedryl acetate | 20 |
| 6 | Citronellyl acetate, 10% in dipropylene glycol | 5 |
| 7 | Cyclopentadecanolide (THIBETOLIDE ®) | 5 |
| 8 | 2,4-Dimethyl-3-cyclohexenecarboxaldehyde (TRICYCLAL ®) | 4 |
| 9 | 2,6-Dimethylhept-5-enal (MELONAL ®), 10% in dipropylene glycol | 7 |
| 10 | 3,7-Dimethyloct-6-en-1-ol (RHODINOL ®) | 35 |
| 11 | Dipropylene glycol | 446.5 |
| 12 | Dodecahydro-3a,6,6,9a-tetramethylnaphtho(2,1b)furan, 10% in dipropylene glycol | 2 |
| 13 | 3,7-Dimethylnona-1,6-dien-3-ol (ethyl linalool) | 50 |
| 14 | 1,4-Dioxacycloheptadecane-5,17-dione (ethylene brassylate) | 5 |
| 15 | 4-Ethyl-3-(4-ethylphenyl)-2,2-dimethylpropanal (FLORALOZONE ®) | 2 |
| 16 | 1,3,4,6,7,8-Hexahydro-4,6,6,7,8,8-hexamethylcyclopenta(g)-2-benzopyran (GALAXOLIDE ®) 50 BB | 150 |
| 17 | Hexyl salicylate | 5 |
| 18 | Alpha-Hexylcinnamaldehyde | 100 |
| 19 | 4-(4-Hydroxy-4-methylpentyl)cyclohex-3-ene-1-carboxaldehyde (CYCLOHEXAL ®) | 25 |
| 20 | Indole, pure, 10% in dipropylene glycol | 3 |
| 21 | cis-Jasmone | 0.5 |
| 22 | Linalool, synthetic | 8 |
| 23 | Methyl dihydrojasmonate | 50 |
| 24 | 1-Methyl-3-(4-(1,1-dimethylethyl)phenyl)propanal (LILIAL ®) | 80 |
| 25 | 8-Methyl-beta-ionone (ISORALDEINE ®) | 35 |
| 26 | 4-Methyl-2-(2-methylpropyl)tetrahydropyran-4-ol (FLOROL ®) | 5 |
| 27 | (4-Methylphenyl)acetaldehyde (SYRINGA ALDEHYDE ®), 10% in diethyl phthalate | 15 |
| 28 | 3-Methyl-5-phenylpentan-1-ol (PHENOXANOL ®) | 10 |
| 29 | Nerol, extra | 15 |
| 30 | 1-(1,2,3,4,5,6,7,8-Octahydro-2,3,8,8-tetramethyl-2-naphthalenyl)ethanone (ISO E SUPER ®) | 20 |
| 31 | (10E)-1-Oxacycloheptadec-10-en-2-one (AMBRETTOLIDE ®) | 10.5 |
| 32 | 1-Phenyleth-1-yl acetate (GARDENOL ®) | 2.5 |
| 33 | Phenylethyl alcohol | 20 |
| 34 | Pepper oil, black | 2 |
| 35 | Rose TW 62/9 Norx | 20 |
| 36 | Alpha-Terpineol (LINDENOL ®) | 5 |
| 37 | 10-Undecen-1-al, 1% in dipropylene glycol | 10 |
| 38 | Mixture II$_2$ | 10 |
| | | 1250 |

The light, clear, crisp lily of the valley character of the compositions containing a mixture of compounds according to formula II$_2$ (i.e., compounds II$_{2a}$ and II$_{2b}$) clearly comes into play in the perfume/cosmetic composition, surprisingly even in this relatively low dosage, and brings elegance and crispness into the olfactory picture and underlines the caring character of the product. The compositions containing a mixture of compounds according to formula II$_2$ may even intensify the effect of other alcohols with less pronounced lily of the valley odor, as shown here by the example of FLOROL®. Neither MAJANTOL®, MAJOL® nor MUGETAMOL® is able to produce in this composition, in like dosages, a similar natural lily of the valley note. Moreover, the mixtures Ia and Ib are also not capable of this.

The invention being thus described, it will be obvious that the same may be varied in many ways. Such variations are not to be regarded as a departure from the spirit and scope of the invention and all such modifications are intended to be included within the scope of the following claims.

What is claimed is:

1. A composition comprising a mixture of compounds having the formula II:

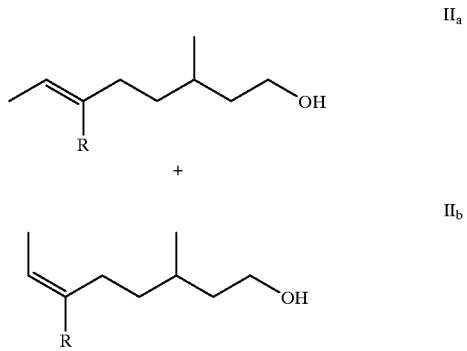

wherein R is methyl or ethyl and which composition is free from the corresponding oct-5-ene double bond isomers.

2. A composition according to claim 1 wherein the compounds are R-enantiomers.

3. A composition according to claim 1 wherein the compounds are S-enantiomers.

4. A composition according to claim 1 wherein the compounds are (6E)-3,6-dimethyloct-6-en-1-ol and (6Z)-3,6-dimethyloct-6-en-1-ol (II$_1$):

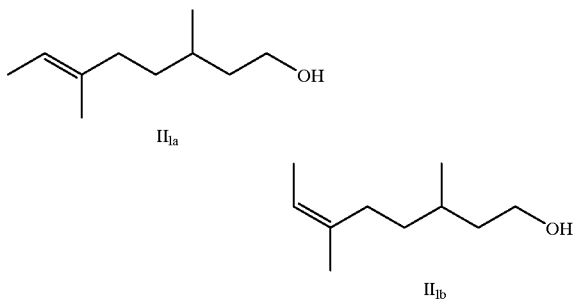

which composition is free from (5E/Z)-3,6-dimethyloct-5-en-1-ol.

5. A composition according to claim 1 wherein the compounds are (6E)-6-ethyl-3-methyloct-6-en-1-ol and (6Z)-6-ethyl-3-methyloct-6-en-1-ol (II$_2$)

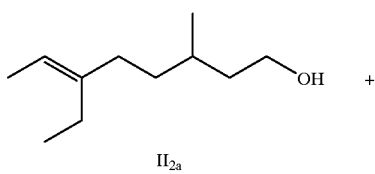

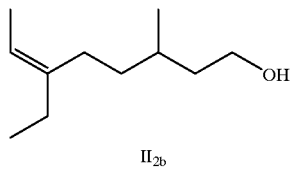

which composition is free from (5E/Z)-ethyl-3-methyloct-5-en-1-ol.

6. An odorant composition comprising a composition according to claim 1.

7. An odorant composition comprising a composition according to claim 4.

8. An odorant composition comprising a composition according to claim 5.

9. A process for preparing an odorant composition for use in a perfume or cosmetic composition comprising mixing an effective amount of a composition according to claim 1 with a perfume or cosmetic base.

10. A process for preparing an odorant composition for use in a perfume or cosmetic composition comprising mixing an effective amount of a composition according to claim 4 with a perfume or cosmetic base.

11. A process for preparing an odorant composition for use in a perfume or cosmetic composition comprising mixing an effective amount of a composition according to claim 5 with a perfume or cosmetic base.

* * * * *